(12) United States Patent
Schoeche et al.

(10) Patent No.: US 10,175,160 B1
(45) Date of Patent: Jan. 8, 2019

(54) METHOD TO ANALYZE SPECTROSCOPIC ELLIPSOMETRY OR INTENSITY DATA OF POROUS SAMPLES UTILIZING THE ANISOTROPIC BRUGGEMAN-EFFECTIVE MEDIUM THEORY

(71) Applicant: J.A. Woollam Co., Inc., Lincoln, NE (US)

(72) Inventors: Stefan Schoeche, Lincoln, NE (US); Jeremy A. Van Derslice, Lincoln, NE (US); Jeffrey S. Hale, Lincoln, NE (US); Craig M. Herzinger, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 0 days.

(21) Appl. No.: 15/932,748

(22) Filed: Apr. 20, 2018

Related U.S. Application Data

(63) Continuation-in-part of application No. 15/731,298, filed on May 22, 2017, now Pat. No. 9,976,902.

(60) Provisional application No. 62/392,242, filed on May 25, 2016.

(51) Int. Cl.
*G01J 4/00* (2006.01)
*G01N 21/21* (2006.01)
*G01J 3/447* (2006.01)
*G01B 11/06* (2006.01)
*G01J 4/04* (2006.01)

(52) U.S. Cl.
CPC ............ *G01N 21/211* (2013.01); *G01B 11/06* (2013.01); *G01J 3/447* (2013.01); *G01J 4/04* (2013.01); *G01N 2021/213* (2013.01)

(58) Field of Classification Search
CPC .......... G01J 3/447; G01J 4/04; G01N 15/088; G01N 15/0806; G01N 21/75; G01N 21/78; G01N 21/211; G01N 2021/213; G06F 17/17; G06F 17/175; G06F 17/12; G06F 17/18; G06G 7/30; G03F 7/0042; G06K 15/225; G01B 11/06; G01B 11/12
See application file for complete search history.

(56) References Cited

U.S. PATENT DOCUMENTS

2017/0315044 A1* 11/2017 Krishnan ............... G01B 11/12

* cited by examiner

*Primary Examiner* — Jamil Ahmed
(74) *Attorney, Agent, or Firm* — James D. Welch

(57) ABSTRACT

Methodology of characterizing pore size distribution in a porous thin film having a surface, or in a surface region of a porous semi-infinite bulk substrate having a surface, involving applying a mathematical model of a sample based on effective medium approaches, such as the Bruggeman effective medium approach.

14 Claims, 7 Drawing Sheets

ANALYSIS. THE BEST MATCHING MODEL IS SHOWN AS DOTTED LINES FOR
THE SAME 5 WAVELENGTHS.

- Graded Layer Thickness #1 = 436.19 nm (MSA)
  Grade Type = Parametric  # of Slices = 10
  Profile = Exponential  Exponent = 0.3637 (fit)
  -Material = PorousEMA
    -Material = Gen-Osc
      Add Oscillator  Show Dialog  Fast Gaussian Calc = ON  ⎫
      Einf = 1.782 (fit)                                                                                  ⎬ Host
      UV Pole Amp. = 20.8290 (fit)  UV Pole En. = 8.000          ⎪ refractive
      IR Pole Amp. = 0.0145 (fit)                                                            ⎭ index
      Fit All  Clear All  Add Amp.  Add Br.  Add En.
    Ambient = Void
    Solvent = h2o high purity 20C
  Total Porosity = (Graded) % Accessible = 100.0 % Filling = 0.0 (MSA)  ⎫
  depolarization (z) = 0.442 (fit) depolarization (x-y split) = 0.500                    ⎬ Anisotropy
  Euler Angles; Phi = 0.00  Theta = 0.00  Psi = 0.00                                  ⎭
  Analysis Mode = Anisotropic Bruggeman
  Grading Parameters: Add  Delete  Delete All  ⎫
                                                                                                                ⎬ Grading
| Name | Value | % Grade | Graph |                                          ⎪ profile
|---|---|---|---|                                                                                         ⎭
| Total Porosity | 40.9 | 1.07 | Draw |

Substrate = Si JAW

FIG. 6

METHOD TO ANALYZE SPECTROSCOPIC ELLIPSOMETRY OR INTENSITY DATA OF POROUS SAMPLES UTILIZING THE ANISOTROPIC BRUGGEMAN-EFFECTIVE MEDIUM THEORY

This Application is a CIP of application Ser. No. 15/731,298 Filed May 22, 2017, and there via Claims benefit from Provisional Application No. 62/392,242 Filed May 25, 2016.

TECHNICAL FIELD

The present invention relates to methods for characterizing pore size and distribution in a porous thin film having an effective thin layer thickness and a surface or a porous surface region of a semi-infinite bulk substrate having a surface, and more particularly to methodology for doing so by applying a mathematical model of a sample based on a Bruggeman effective medium.

BACKGROUND

Porous materials are widely applied in science and engineering with applications including filtration devices, acoustic and thermal insulation materials, low-k dielectrics in microelectronic devices, ultra-light materials, catalysts, ion exchange materials, optical coatings, photovoltaics, sensing devices and many more. Porous materials consist of a skeletal portion often referred to as matrix or host material and pores which are filled with a fluid, either liquids or gases. The medium is characterized by its total porosity, i.e., the volume fraction of empty or filled space in relation to the overall material volume. Depending on the applications, additional characteristics can be of interest such as the pore diameter and the specific surface area, i.e., the total surface area including pores relative to a unit of mass or volume. The overall mechanical (eg. tensile strength, strain), optical (high-frequency permittivity), and magneto-electric (low-frequency permittivity, conductivity, permeability etc.) properties of the porous material are a result of the combined properties of its constituents and can often be approximated using effective medium theories. Due to the complicated microstructure, these effective properties often vary within the material resulting, for example, in anisotropic optical and electronic properties, or gradients in pore size and overall porosity.

Porous materials are classified according to IUPAC notation as microporous for average pore diameters below 2 nm, mesoporous for pore diameters between 2-50 nm, and macroporous for pore diameters above 50 nm. The most common technique to characterize the overall porosity and pore size distribution in mesoporous and microporous samples is $N_2$ adsorption porosimetry which determines adsorption and desorption isotherms for bulk porous samples of large volume by directly measuring the weight increase/decrease due to adsorption/desorption of liquid ($N_2$) on/from the pore walls (for macroporous samples, high-pressure mercury porosimetry is commonly applied, but macroporous samples are not topic of this investigation). The calculation of the pore size distribution in mesoporous samples assumes progressive (instantaneous) filling and emptying of porous systems of a specific pore size at adsorbate (here $N_2$) partial pressures below the saturation vapor pressure of that solvent for flat surfaces, $P_0$. The dependence of the relative pressure $P/P_0$ at which condensation in pores occurs on the meniscus curvature is given by the Kelvin equation:

$$\ln\left(\frac{P}{P_0}\right) = -\frac{f\gamma V_m \cos\theta}{r_k RT} \quad (1)$$

where $\gamma$ and $V_m$ are the surface tension and molar volume of the liquid solvent (adsorbate), $\theta$ is the contact angle of the liquid solvent on a non-porous surface of the host material, R is the molar gas constant, T is the temperature in K, and f is a shape factor equal to 1 for slit-shaped pores and equal to 2 for cylindrical pores, respectively. The quantity $r_K$ is the Kelvin radius, which is related to the actual pore radius, $r_p$, by $r_p = r_k + t$ where t is the thickness of the layer adsorbed on the pore walls shortly before condensation occurs. The parameter t describes the observation that some amount of solvent will adsorb to any surface and form thin (partial) layers in dependence of the relative pressure and can be either determined by measuring the thickness of the adsorbed solvent vs. relative pressure on a flat non-porous surface of the same material or estimated from the Brunauer, Emmet, Teller (BET) equation. FIG. 1 shows the typical hysteresis loop of the determined condensed solvent volume within the pores of a mesoporous $SiO_2$ in dependence of the relative solvent pressure which is a result of different effective radius of curvature of the condensed liquid meniscus during adsorption and desorption.

Microporous samples with pore diameters smaller than 2 nm show significant variation of the optical properties of the sample for relative pressures $P/P_0 < 0.1$. The theory describing the variation of condensed solvent volume within the micropores in dependence of the relative solvent pressure is based on the assumption of micropore volume filling rather than layer-by-layer adsorption on pore walls (Dubinin-Radushkevitch theory) which will not be further outlined here. The pore size distribution for a porous sample can be determined by analyzing the dependence of the condensed solvent volume on the relative pressure $P/P_0$. Under the assumption that all pores of the same radius are filled or emptied more or less instantaneous when the condition of the Kelvin equation are met, then the pore size distribution can be determined by calculating the derivate of the condensed solvent volume in the pores vs. relative pressure. The corresponding pore radii are calculated from the relative pressure values $P/P_0$ by applying Eq. (1). (Note at this point, that FIG. 1 shows Typical hysteresis of the adsorbed solvent (water) volume for an adsorption/desorption cycle on a mesoporous $SiO_2$ film on Si, and FIG. 2 shows Pore size distribution for the example of porous $SiO_2$ on Si shown in FIG. 1).

Pore Size Analysis from Spectroscopic Ellipsometry or Intensity Data Using the Established Lorentz-Lorenz Equation Approach The basic idea of using spectroscopic ellipsometry or intensity data for determining structural properties of porous samples is to monitor the change of optical properties due to condensation of solvent within the pores rather than measuring absolute weight of condensed solvent which would be difficult for thin film samples. Spectroscopic ellipsometry accurately determines the optical properties of a sample with change of the relative solvent pressure and can simultaneously monitor variations of the thickness for thin film samples. Spectroscopic ellipsometry is an indirect technique which requires an optical model for which relevant parameters are varied during a regression analysis in order to best match the experimental data. The variation of the optical properties of a porous sample can be related to the amount of condensed solvent within the pores by applying effective medium theories. Several different models were derived based on certain assumptions on microstructural mixing of constituents. For pore diameters much smaller than the wavelength of the probing light beam, good agreement between the derived fractions of skeletal material, void, and potential other constituents (such as a partial fill by a liquid) with the same quantities determined by alternative experimental techniques has been demonstrated. To determine the pore size distribution, experimental spectroscopic ellipsometry or intensity data has to be acquired over a wide relative pressure range in order to obtain the characteristic hysteresis loop observed in a standard adsorption measurement. An appropriate procedure to obtain the desired condensed solvent volume within the pores from the spectropic ellipsometry, (or intensity), data for different relative solvent pressure values has to be chosen.

A procedure based on the Lorentz-Lorenz effective medium theory is well documented in literature. The Lorentz-Lorenz model is an extension of the Clausius-Mosotti equation for the polarizability of spherical particles in air assuming multiple particle species which are homogeneously mixed on the microscopic scale:

$$\frac{\varepsilon - 1}{\varepsilon + 2} = f_a \frac{\varepsilon_a - 1}{\varepsilon_a + 2} + (1 - f_a) \frac{\varepsilon_b - 1}{\varepsilon_b + 2} \quad (2)$$

For effective mediums consisting of a skeletal material with some void space neither the assumption of a microscopic mix nor the matrix being air is a good assumption. Therefore, this model is typically not used to analyze ellipsometric or intensity data. However, the equation was adopted in the porosimetry field since it can be used to derive a very simple equation to describe the condensed solvent volume in porous samples at a specific relative pressure. The polarizability P for the three cases of a solid film ($n_s$), empty porous films ($n_e$), (see FIG. 9A), filled with air ($n_0$=1), (see FIG. 9B), and porous film ($n_{rel}$) partially filled with solvent ($n_{sol}$), (see FIG. 9C), are given by, respectively:

$$P = \frac{n_s^2 - 1}{n_s^2 + 2};$$

$$P = \frac{n_e^2 - 1}{n_e^2 + 2} = V_1 \frac{n_0^2 - 1}{n_0^2 + 2} + (1 - V_1) \frac{n_s^2 - 1}{n_s^2 + 2} = (1 - V) \frac{n_s^2 - 1}{n_s^2 + 2};$$

$$P\left(\frac{P}{p_0}\right) = \frac{n_{rel}^2 - 1}{n_{rel}^2 + 2} = V_1 \frac{n_0^2 - 1}{n_0^2 + 2} + V_2 \frac{n_{sol}^2 - 1}{n_{sol}^2 + 2} + (1 - V_1 - V_2) \frac{n_s^2 - 1}{n_s^2 + 2}.$$

(Where V . . . =Total Porosity).

Under the assumption that the sum of the empty volume $V_1$ and the condensed solvent volume $V_2$ in the partially filled pores equals the total porosity V of the empty pores, the last two equations can be combined and rearranged in order to determine the solvent volume $V_2$ in the pores at arbitrary filling state, i.e., at any relative pressure ($P/P_0$):

$$V_2\left(\frac{P}{P_0}\right) = \left(\frac{n_{rel}^2 - 1}{n_{rel}^2 + 2} - \frac{n_e^2 - 1}{n_e^2 + 2}\right) / \frac{n_{sol}^2 - 1}{n_{sol}^2 + 2} \quad (3)$$

This equation only depends on the homogenous layer refractive index determined for the case of empty pores ($n_e$ at $P/P_0$=0), the known solvent refractive index $n_{sol}$, and the homogenous layer refractive index $n_{rel}$ determined at that specific relative pressure. $n_{rel}$ and $n_e$ refer to the refractive indices derived from a model analysis under the assumption that the porous material can be described as one homogeneous solid layer of equivalent optical properties.

The ellipsometric or intensity data analysis is performed step-by-step for each time slice of an adsorption or desorption cycle (scan over wide relative pressure range. An appropriate optical model has to be chosen to describe the optical properties of the porous layer (In many cases, a simple Cauchy model for transparent films will be sufficient to match the data). The user has to identify a refractive index value to use for the condensed solvent volume calculation according to Eq. (3). In most cases, this will be the refractive index value at a specific wavelength, i.e., the spectroscopic nature of the experiment is completely ignored. For this approach, the sample has to be isotropic. Further, all time slices are modeled independent of any other time slice. Therefore, noise or non-idealities not accounted for in the ellipsometric model will directly transfer to noise in the determined condensed solvent volume. The total porosity is adopted from the resulting solvent volume curve vs. relative pressure by extrapolation to the relative pressure $P/P_0$=1 under the assumption that all pores are filled at that pressure. Potential isolated pore volumes (not accessible by solvent) are ignored. The pore size distribution is determined from the solvent volume vs. relative pressure plots.

Advantages of the Lorentz-Lorenz equation formalism:
Skeletal material refractive index does not need to be known;
Very simple, only needs single-wavelength refractive index values;

Disadvantages:
Based on invalid assumptions on microscopic nature of the film;
Randomly uses single-wavelength refractive indices despite analyzing spectroscopic data (which one to choose?);
Only applicable to isotropic and homogenous materials, however, most porous films show out-of-plane anisotropy (pore shape) or graded properties (porosity)
Assumes completely empty pores at $P/P_0$=0 and filled pores at $P/P_0$=1;
No access to isolated pore volume and refractive index of the skeletal material.

Despite being a fairly simple approach, useful data can be obtained by using the Lorentz-Lorenz equation formalism. However, in many cases only mediocre match between model and experimental data will be achieved. In this case, it is not possible to predict what error is present in the determined solvent volume considering the fact that the model is not capable of matching the experimental data.

Known patents in the area are U.S. Pat. No. 9,423,447 to Kiermasz, and U.S. Pat. No. 5,248,614 to Wang.

Even in view of the prior art, need remains for a method of determining pore size and distribution in an effective thin layer, or a surface region of a ocmi-infinite infinite bulk substrate based on applying a Bruggeman effective medium model that follows physically motivated and accurate ellipsometric, (or intensity) data analysis. In particular need remains for a method which can account for the anisotropic nature of an effective layer on a substrate, can access pore volume, account for graded sample properties and does not rely on assumptions about the pore filling state at any given relative solvent pressure.

DISCLOSURE OF THE INVENTION

The present invention is a method of determining the distribution of pore size distribution vs. radius in a porous sample selected from the group consisting of:
1) a porous thin film having an effective thin layer thickness and a surface; and
2) a porous surface region of a semi-infinite bulk substrate having a surface.

Said method comprises the steps of:
a) providing a selection from the group consisting of:
 1) a reflectometer comprising a source of electromagnetic radiation, a stage for supporting a sample and a detector of electromagnetic radiation; and
 2) an ellipsometer or polarimeter comprising a source of electromagnetic radiation, a polarizer, a stage for supporting a sample, an analyzer and a detector of electromagnetic radiation, said ellipsometer or polarimeter optionally comprising at least one compensator between said source and detector.

Said method continues with:
b) placing a selected sample on said stage and while causing said surface of said sample to undergo a sequential plurality of solvent relative pressures, causing said selected reflectometer, ellispometer or polarimeter to direct a beam of electromagnetic radiation at said sample, so that it interacts therewith and enters said detector which mediates the development of a set of reflectometer or ellipsometer or polarimeter data;
c) before, after or simultaneous with step b) providing a mathematical model of said selected sample which includes as parameters a plurality of filling fractions as a function of solvent relative pressure;
d) performing a regression procedure of said mathematical model provided in step c) onto at least some of said data determined in step b) to determine data corresponding to an effective plot of filling fraction vs. solvent relative pressures; and
e) performing a differentiation of said effective plot of filling fraction vs. solvent relative pressures determined in step d), to provide an effective plot of pore size distribution vs. radius.

It is to be noted that numerical differentiation of data can amplify noise and artifacts, hence, while workable, practicing the foregoing method can be prone to difficulties. A method that does not require differentiation, but rather utilizes integration of data during a regression procedure would therefore provide utility.

With that in mind, the present invention is also a method of determining the distribution of pore size distribution vs. radius in a porous sample selected from the group consisting of:
1) a porous thin film having an effective thin layer thickness and a surface; and
2) a porous surface region of a semi-infinite bulk substrate having a surface;

Said method comprises the steps of:
a) providing a selection from the group consisting of:
 1) a reflectometer comprising a source of electromagnetic radiation, a stage for supporting a sample and a detector of electromagnetic radiation; and
 2) an ellipsometer or polarimeter comprising a source of electromagnetic radiation, a polarizer, a stage for supporting a sample, an analyzer and a detector of electromagnetic radiation, said ellipsometer or polarimeter optionally comprising at least one compensator between said source and detector.

Said method continues with:
b) placing a selected sample on said stage and while causing said surface of said sample to undergo a sequential plurality of solvent relative pressures, causing said selected reflectometer, ellispometer or polarimeter to direct a beam of electromagnetic radiation at said sample, so that it interacts therewith and enters said detector which mediates the development of a set of reflectometer or ellipsometer or polarimeter data;
c) before, after or simultaneous with step b) providing a mathematical model of said selected sample which includes as parameters a plurality of filling fractions as a function of solvent relative pressure, and further provides a parameterized representation of an effective plot of pore size distribution vs. radius;
d) performing a regression procedure of said mathematical model provided in step c) onto at least some of said data determined in step b) to simultaneously determine best fit values for the parameters in said effective plot of pore size distribution vs. radius, and an effective plot of filling fraction vs. solvent relative pressures which is arrived at by an integration of said parameterized representation of an effective plot of pore size distribution vs. radius, during said regression.

In either method said sample can comprise skeletal material presenting with a total volumetric porosity %, a % of total pores present in the volume of said thin film which are accessible by solvent presented at said surface thereof, and a % of accessible pores actually filled with solvent at a plurality of times during which the partial pressure of said solvent, relative to the saturation vapor pressure of said solvent over any flat surface, is changed at said sample surface, and wherein the mathematical model of said sample is a Bruggeman effective medium model including as parameters therein, at least:
 variable wavelength dependent refractive index of said skeletal material;
 variable total porosity %;
 variable % of accessible pores that are filled with solvent at a given partial pressure, (ie. volume filling plot); and
 wavelength dependent refractive index values of said solvent;

and can optionally further as model parameters at least one selection from the group:
 variable % of accessible pores;
 if the sample is a thin film, a thickness parameter therefore; and/or
 variable grading profile of any of the mathematical model parameters over the investigated thickness of said sample; and/or
 at least one variable depolarization factor; and
 wherein while assuming fixed values for wavelength dependent solvent refractive indices, and for at least one selection from the group consisting of:
 100% of all pores are assumed accessible; and
 the wavelength dependent refractive indices of said skeletal material are known.

Either method can further involve that the plurality of ellipsometric or intensity data sets obtained in step b) are spectroscopic and the regression in step d) involves at least two thereof for each of said plurality of ellipsometric or intensity data sets that correspond to a plurality of times corresponding to different solvent partial pressures being presented to the surface of said sample.

Either method can further involve that the plurality of ellipsometric or intensity data sets obtained in step b) are obtained during solvent adsorption or desorption within the sample pores for a plurality of times during which the partial pressure of said solvent is increased or decreased at said sample surface respectively, or during an adsorption-desorptinn hysteresis cycle during which the partial pressure of said solvent is increased and decreased at said sample surface.

Either method can provide that the plurality of ellipsometric or intensity data sets obtained in step b) are obtained during solvent adsorption or desorption at said sample surface for a plurality of times during which the partial pressure of said solvent is increased or decreased at said sample surface respectively, which further comprises determining pore size distribution involving use of a derivative of a volume filling plot vs. partial pressure.

Either method can involve that data is obtained in step b) during an adsorption-desorption hysteresis cycle during which the partial pressure of said solvent is both increased and decreased at said sample surface within a partial range between zero and saturation partial pressure.

Either method can involve that data is obtained in step b) during an adsorption-desorption hysteresis cycle during which the partial pressure of said solvent is both increased and decreased at said sample surface within a full range between zero and saturation partial pressure, at which none, and at which all pores are filled, respectively.

Either method can involve a variable grading profile of any of the mathematical model parameters over the investigated thickness of said sample; and/or a variable depolarization factor are included in the model if that inclusion provides better fit of parameters when said step d) regression is performed.

Either method can involve that the wavelength dependent values of skeletal material refractive index are known and fixed, and variable % of accessible pores is a variable, or in which the wavelength dependent values of skeletal material refractive index are variable, and variable % of accessible pores is fixed and the remaining variable parameters are fit parameters.

Either method can involve that the wavelength dependent values of skeletal material refractive index are fixed, 100% of pores are assumed accessible, and the remaining variable parameters are fit parameters.

The present invention is based in a method previously disclosed in Allowed application Ser. No. 15/731,298 Filed May 22, 2017, which Claimed benefit from Provisional Application No. 62/392,242 Filed May 25, 2016. The disclosure from that Application is included herein directly.

The previously disclosed invention is based in a method of enabling determination of pore size and distribution in a sample selected from the group consisting of:
    a porous thin film having an effective thin layer thickness and a surface; and
    a porous surface region of a semi-infinite bulk substrate having a surface;
said sample comprising skeletal material presenting with a total volumetric porosity %, a % of total pores present in the volume of said thin film which are accessible by solvent presented at said surface thereof, and a % of accessible pores actually filled with solvent at a plurality of times during which the partial pressure of said solvent, (relative to the solvation pressure of said solvent over any flat surface), is changed at said sample surface, said method involving obtaining ellipsometric or intensity data at a plurality of times while partial pressure of said solvent is changed in the vicinity of the surface of said sample, and performing a simultaneous regression on said ellipsometric or intensity data obtained at at least two of said times, said method not requiring knowledge of effective refractive index values of said porous thin film having an effective thin layer thickness or said porous surface region of a semi-infinite bulk substrate when all pores therein contain no solvent and when they are essentially completely filled.

Said method comprises:
a) providing an ellipsometer system comprising a source of electromagnetic radiation, a polarization state generator, a stage for supporting a sample in a chamber that enables controlling the partial pressure of said solvent at the surface of said sample, a polarization state analyzer and a detector of electromagnetic radiation;
b) while causing said surface of sample to undergo a sequential plurality of solvent partial pressures adjacent thereto in said chamber, obtaining a plurality of ellipsometric or intensity data sets that correspond to a plurality of times corresponding to different solvent partial pressures being presented to the surface of said sample;
c) simultaneous with, or after step a), providing a mathematical model of said sample as a Bruggeman effective medium including as parameters therein, at least:
    variable wavelength dependent refractive index of said skeletal material;
    variable total porosity %;
    variable % of accessible pores that are filled with solvent at a given partial pressure, (ie. volume filling); and
    wavelength dependent refractive index values of said solvent;
and optionally further including as model parameters:
    variable % of accessible pores;
    if the sample is a thin film, a thickness parameter therefore; and/or
    variable grading profile of any of the mathematical model parameters over the investigated thickness of said sample; and/or
    at least one variable depolarization factor; and
d) while assuming fixed values for wavelength dependent solvent refractive indices, and for at least one selection from the group consisting of:
    100% of all pores are assumed accessible; and
    the wavelength dependent refractive indices of said skeletal material are known;
performing a simultaneous regression on at least two of the plurality of ellipsometric or intensity data sets obtained in step b) onto the mathematical model in step c) for said sample to obtain best fit values for the remaining fit parameters in step c).

Said method can involve the plurality of ellipsometric, or intensity data sets obtained in step b) are spectroscopic and the regression in step d) involves at least two thereof for each of said plurality of ellipsometric or intensity data sets that correspond to a plurality of times corresponding to different solvent partial pressures being presented to the surface of said sample.

Said method can involve the plurality of ellipsometric or intensity data sets obtained in step b) are obtained during solvent adsorption or desorption within the sample pores for a plurality of times during which the partial pressure of said solvent is increased or decreased at said sample surface respectively, or during an adsorption-desorption cycle during which the partial pressure of said solvent is increased and decreased at said sample surface.

Said method can involve the plurality of ellipsometric or intensity data sets obtained in step b) are obtained during solvent adsorption or desorption at said sample surface for a plurality of times during which the partial pressure of said solvent is increased or decreased at said sample surface respectively, which further comprises determining pore size distribution involving use of a derivative of a volume filling plot vs. partial pressure.

Said method can involve data is obtained in step b) during an adsorption-desorption hysteresis cycle during which the partial pressure of said solvent is both increased and decreased at said sample surface within a partial range between zero and saturation partial pressure.

Said method can involve that data is obtained in step b) during an adsorption-desorption hysteresis cycle during which the partial pressure of said solvent is both increased and decreased at said sample surface within a full range between zero and saturation partial pressure, at which none, and at which all pores are filled, respectively.

Said method can further comprise determining pore size distribution by taking a derivative of a volume filling plot vs. partial pressure.

Said method can involve the variable grading profile of any of the mathematical model parameters over the investigated thickness of said sample; and/or a variable depolarization factor being included in the model if that inclusion provides better fit of parameters when said step d) regression is performed, thereby accounting for the anisotropic nature of the sample.

Said method can involve that the wavelength dependent values of skeletal material refractive index are known and fixed, and variable % of accessible pores is a variable, or in which the wavelength dependent values of skeletal material refractive index are variable, and variable % of accessible pores is fixed and the remaining variable parameters are fit parameters.

Said method can involve that the wavelength dependent values of skeletal material refractive index are fixed, 100% of pores are assumed accessible, and the remaining variable parameters are fit parameters.

The previously disclosed invention is further an alternative method of enabling determination of pore size and distribution in a sample selected from the group consisting of:
 a porous thin film having an effective thin layer thickness and a surface; and
 a porous surface region of a semi-infinite bulk substrate having a surface;
said sample comprising skeletal material presenting with a total volumetric porosity %, a % of total pores present in the volume of said thin film which are accessible by solvent presented at said surface thereof, and a % of accessible pores actually filled with solvent, expressed as fraction of skeletal material, fraction of solvent and fraction of void, at a plurality of times during which the partial pressure of said solvent is changed at said sample surface, said method involving obtaining ellipsometric or intensity data at a plurality of times while partial pressure of a solvent is changed in the vicinity of the surface of said sample, and performing a simultaneous regression on said ellipsometric or intensity data obtained at at least two of said times, said method not requiring knowledge of effective refractive index values of said porous thin film having an effective thin layer thickness or said porous surface region of a semi-infinite bulk substrate when all pores therein contain no solvent and when they are essentially completely filled.
Said method comprises:
a) providing an ellipsometer system comprising a source of electromagnetic radiation, a polarization state generator, a stage for supporting a sample in a chamber that enables controlling the partial pressure of said solvent at the surface of said sample, a polarization state analyzer and a detector of electromagnetic radiation;
b) while causing said surface of sample to undergo a sequential plurality of solvent partial pressures adjacent thereto in said chamber, obtaining a plurality of ellipsometric or intensity data sets that correspond to a plurality of times corresponding to different solvent partial pressures being presented to the surface of said sample;
c) simultaneous with, or after step a), providing a mathematical model of said sample as a Bruggeman effective medium including as parameters therein, at least:
 skeletal material fraction;
 solvent fraction;
 void fraction;
 refractive index of said skeletal material;
 wavelength dependent refractive index values of said solvent;
 wavelength dependent refractive index values of said void;
and optionally further including as model parameters:
 if the sample is a thin film, a thickness parameter therefore; and/or
 variable grading profile of any of the mathematical model parameters over the investigated thickness of said sample; and/or
 at least one variable depolarization factor; and
d) while assuming fixed values for wavelength dependent solvent refractive indices and for said fraction of skeletal material and for said fraction of void, performing a simultaneous regression on at least two of the plurality of ellipsometric or intensity data sets obtained in step b) onto the mathematical model in step c) for said sample to obtain best fit values for the remaining fit parameters in step c).

Said alternative method can involve the plurality of ellipsometric or intensity data sets obtained in step b) are spectroscopic and the regression in step d) involves at least two thereof for each of said plurality of ellipsometric or intensity data sets that correspond to a plurality of times corresponding to different solvent partial pressures being presented to the surface of said sample.

Said alternative method can involve the plurality of ellipsometric or intensity data sets obtained in step b) are obtained during solvent adsorption or desorption within the sample pores for a plurality of times during which the partial pressure of said solvent is increased or decreased at said sample surface respectively, or during an adsorption-desorption hysteresis cycle during which the partial pressure of said solvent is increased and decreased at said sample surface.

Said alternative method can involve the plurality of ellipsometric or intensity data sets obtained in step b) are obtained during solvent adsorption or desorption at said sample surface for a plurality of times during which the partial pressure of said solvent is increased or decreased at said sample surface respectively, which further comprises determining pore size distribution involving use of d derivative of a volume filling plot vs. partial pressure.

Said alternative method can involve that data is obtained in step b) during an adsorption-desorption hysteresis cycle during which the partial pressure of said solvent is both increased and decreased at said sample surface within a partial range between zero and saturation partial pressure.

Said alternative method can involve that data is obtained in step b) during an adsorption-desorption hysteresis cycle during which the partial pressure of said solvent is both increased and decreased at said sample surface within a full range between zero and saturation partial pressure, at which none, and at which all pores are filled, respectively.

Said alternative method can involve that a variable grading profile of any of the mathematical model parameters over the investigated thickness of said sample; and/or a variable depolarization factor are included in the model if that inclusion provides better fit of parameters when said step d) regression is performed.

Said alternative method can further comprise determining pore size distribution by taking a derivative of solvent fraction vs. partial pressure.

Either method can involve that at least one of:
said variable wavelength dependent refractive index of said skeletal material;
said wavelength dependent refractive index values of said solvent;
said wavelength dependent refractive index values of said void;
is determined using a multiplicity of measurements simultaneously.

Either method can involve that three variable depolarization factors are included in said Bruggman effective medium approximation mathematical model.

Further, either method can involve that data obtained at a multiplicity of times are analyzed simultaneously to extract information about solvent fraction or volume at a multiplicity of partial pressures and where the applied effective medium approximation is selected from the group consisting of:
the group of Maxwell-Garnet approximation;
the Lorentz-Lorenz approximation; and
a linear combination of refractive indices based on solvent fraction, skeletal material fraction and void fraction.

In the foregoing it is to be understood that the mathematical model provided in step c) can further provide that said selected sample is modeled as comprising a plurality of layers, each said layer being characterized by at least one parameter which is separately evaluated in step d) to be: the same as; or different from those in other layers; thereby providing a graded relationship of said at least one parameter as a function of layer position in said sample. While not limiting, said layers can each include as said at least one parameter, at least one selection from the group consisting of: total porosity; % of accessible pores; and depolarization factor. Other parameters can also be present.

The present invention will be better understood by reference to the Detailed Description of this Specification, in combination with the Drawings.

BRIEF DESCRIPTION OF THE DRAWINGS

FIG. 6 shows Best-matching Graded Anisotropic Bruggeman EMA layer for the porous $SiO_2$ on Si example. A Sellmeier model ("Gen-Osc") is selected in the "Material" section to obtain the transparent skeletal material optical constants from the multi-time analysis.

Figure 1:
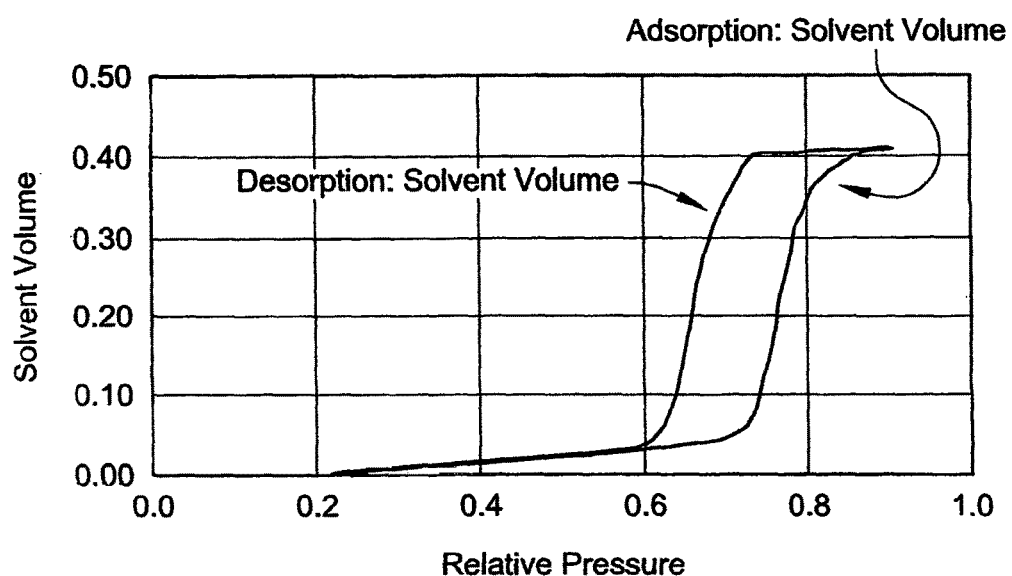
FIG. 1 shows Typical hysteresis of the adsorbed solvent (water) volume for an adsorption/desorption cycle on a mesoporous $SiO_2$ film on Si.

$$P = \frac{n_s^2 - 1}{n_s^2 + 2};$$

$$P = \frac{n_e^2 - 1}{n_e^2 + 2} = V_1 \frac{n_0^2 - 1}{n_0^2 + 2} + (1 - V_1)\frac{n_s^2 - 1}{n_s^2 + 2}; = (1 - V)\frac{n_s^2 - 1}{n_s^2 + 2}$$

and $$P\left(\frac{p}{p_0}\right) = \frac{n_{rel}^2 - 1}{n_{rel}^2 + 2} = V_1 \frac{n_0^2 - 1}{n_0^2 + 2} + V_2 \frac{n_{sol}^2 - 1}{n_{sol}^2 + 2} + (1 - V_1 - V_2)\frac{n_s^2 - 1}{n_s^2 + 2};$$

(where V . . . Total porosity).

DETAILED DESCRIPTION

Turning now to the Drawings, FIGS. 1-9C demonstrate a Novel method for Pore size analysis from spectroscopic ellipsometry or intensity data based on the anisotropic Bruggeman effective medium approach. In which a novel data analysis approach based on the anisotropic Bruggeman effective medium approximation (EMA) which overcomes all disadvantages of the Lorentz-Lorenz approach and accurately describes the nature of the porous film, while providing best match between model and experimental data.

Standard effective medium approaches such as the Bruggeman EMA have been shown to accurately determine the volume fraction in porous mediums consisting of a host material (skeletal, $n_s$), void (n=1), and/or additional constituents such as a liquid of known refractive index in the pores (liquid index, $n_1$). The direct result of such analysis is a value for the condensed solvent volume vs. relative pressure. However, said Bruggeman EMA approach has not previously been applied to determining pore size and distribution in thin films or surface regions of semi-infinite bulk samples.

The Anisotropic Bruggeman EMA (ABEMA) approach can be used to account for the optical anisotropy observed in many porous films due to the shape of the pores or the pore network. This method creates an anisotropic dielectric function tensor from the three isotropic, bulk refractive index values of the host material, the ambient which in most cases is simply air (n=1), and the adsorbate (solvent), by using so-called "depolarization factors" $L_j$ along the three axes of a Cartesian sample coordinate system and by mixing those according to the fraction $f_n$ of each constituent in the effective medium. The sum of the depolarization factors must equal unity. The effective dielectric function tensor element $\varepsilon_{eff,j}$ along direction j=x, y, z is implicitly calculated from:

$$\sum_{n=1}^{m} f_n \frac{\varepsilon_n - \varepsilon_{\mathit{eff},j}}{\varepsilon_{\mathit{eff},j} + L_j(\varepsilon_n - \varepsilon_{\mathit{eff},j})} = 0 \quad (4)$$

$\varepsilon_n$ is the isotropic refractive index of each constituent (as bulk). The result of this calculation is an anisotropic dielectric function tensor with the anisotropy solely caused by the shape of the pores or pore network as described by the three wavelength-independent depolarization factors. For most porous samples, potential local in-plane anisotropy averages out over a larger area and the samples appear isotropic when rotated relative to the plane of incidence of the ellipsometer. However, anisotropy along the surface normal is often observed. Consequently, the depolarization factor $L_z$ will differ from 0.333 (isotropic value), with the remaining $(1-L_z)$ being split equally for $L_x$ and $L_y$.

Figure 3:
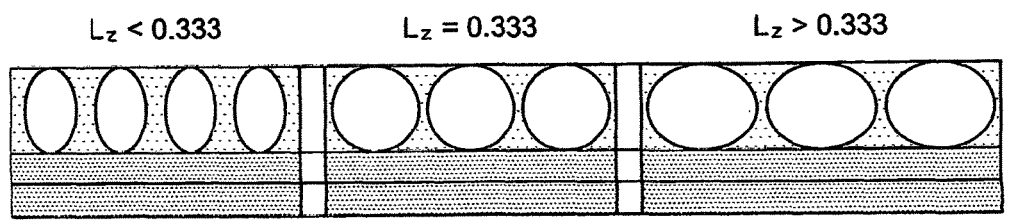
FIG. 3 shows exaggerated and idealized schematic representation of the pore or pore network shape for different depolarization parameter values.
Figure 4:
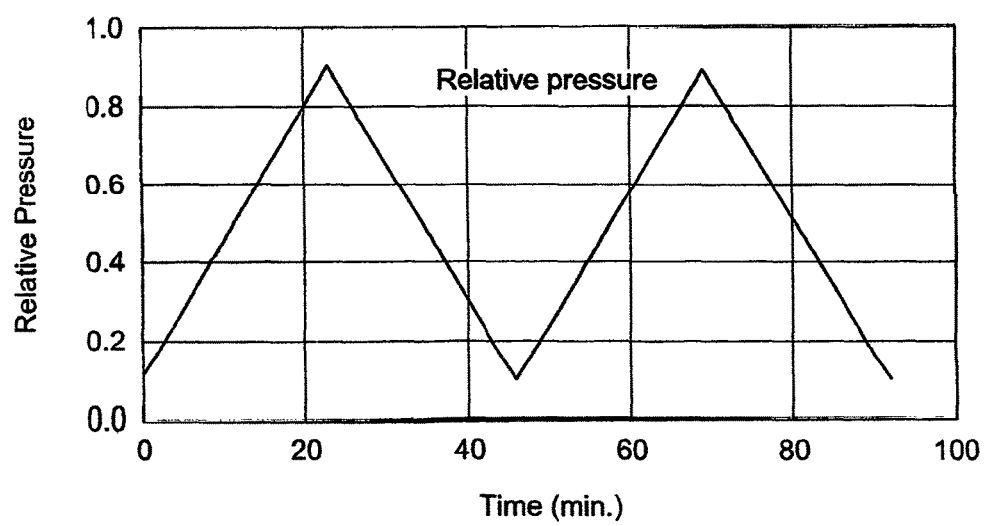
FIG. 4 shows Relative Pressure vs. Time for two Adsorption/Desorption cycles.
Figure 5:
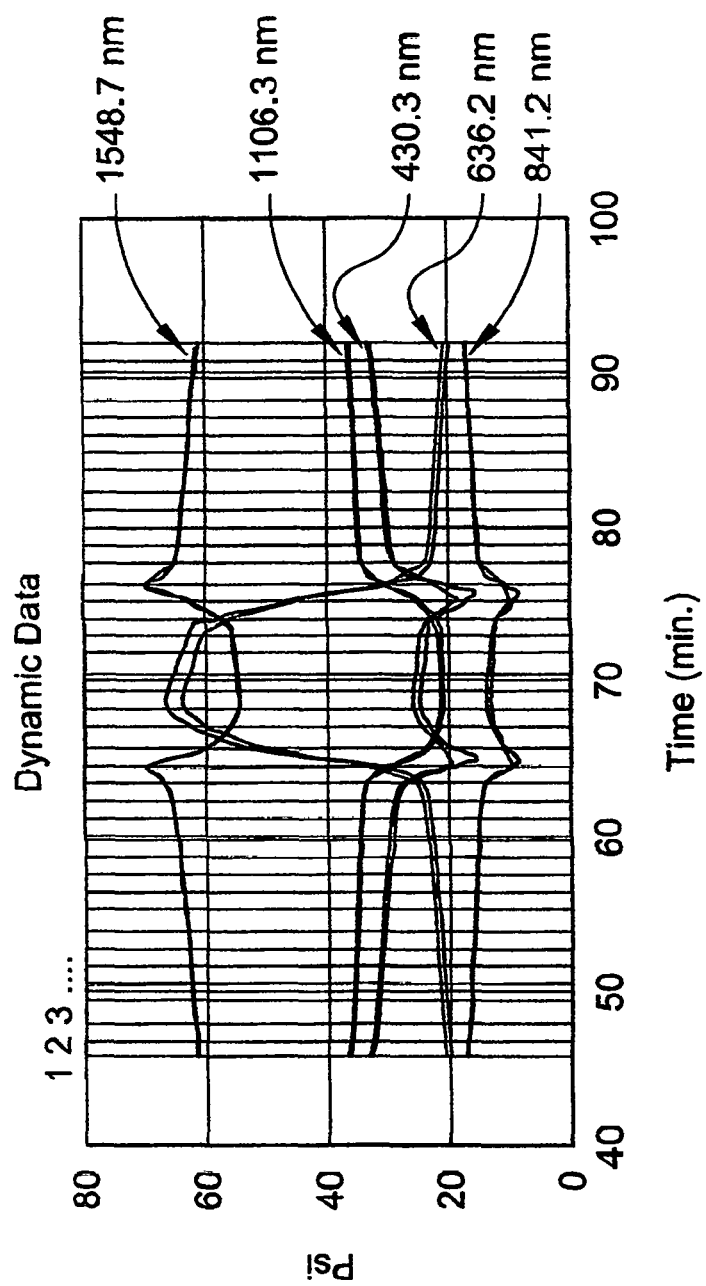
FIG. 5 shows Forty Multi-time slice points selected over an Adsorption-Desorption cycle for a porous SiO2 film on Si substrate.
Figure 7A:
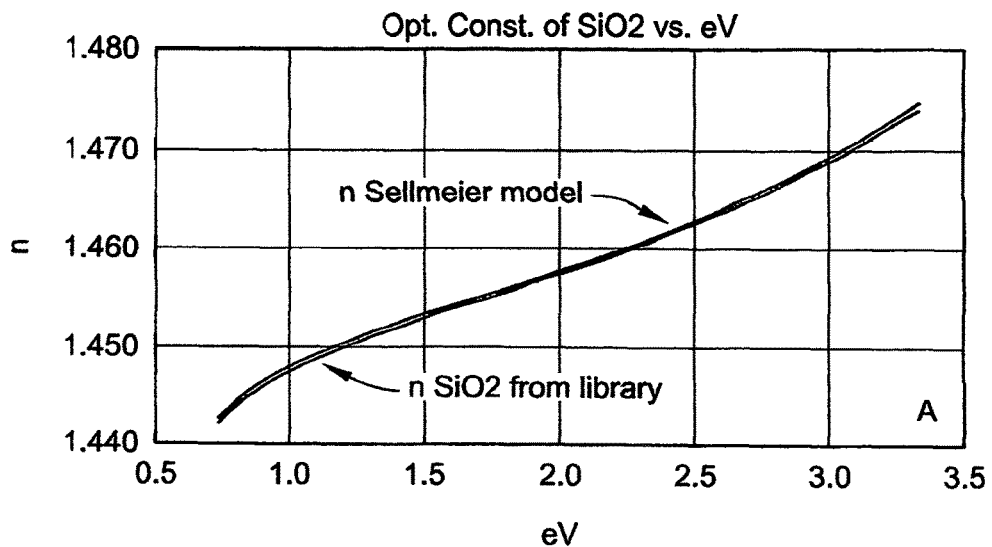
FIGS. 7a and 7b show, respectively, "bulk-like" optical constants for the $SiO_2$ skeletal material as determined form the Multi-Time slice analysis in comparison to the library optical constants of $SiO_2$ (7a), and grading profile for our porous $SiO_2$ on Si example (7b).
Figure 7B:
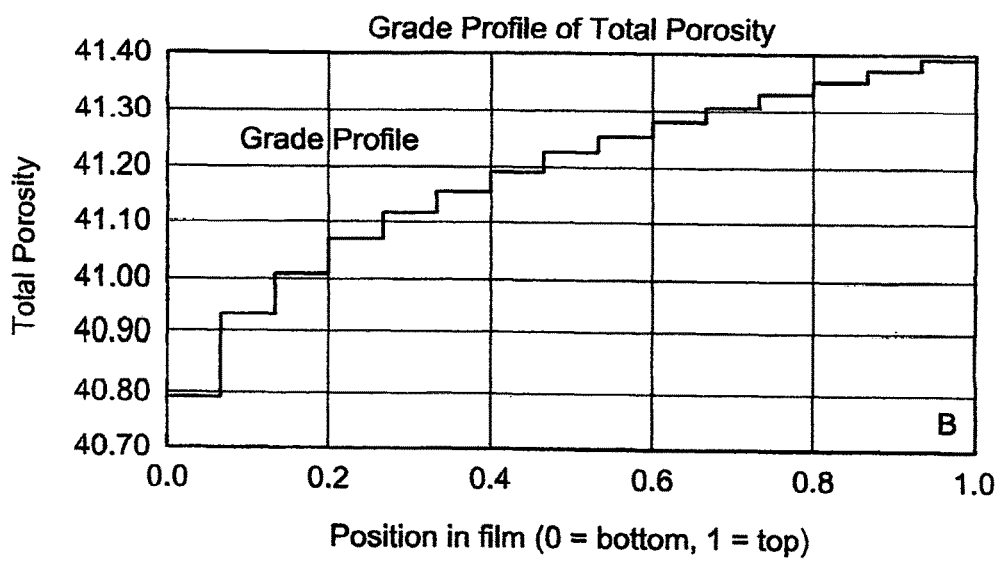
Figure 8A:
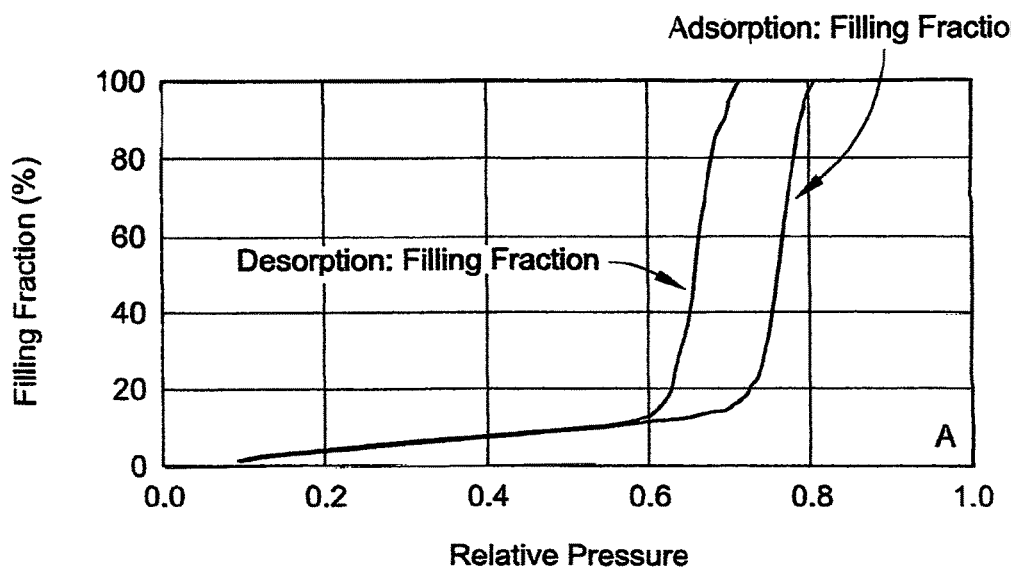
FIGS. 8a and 8b show, respectively, Condensed Solvent volume ("% Filling" of total porosity) vs. relative pressure, and resulting pore size distribution for the porous $SiO_2$ on Si example derived using the anisotropic Bruggeman EMA model.
Figure 8B:
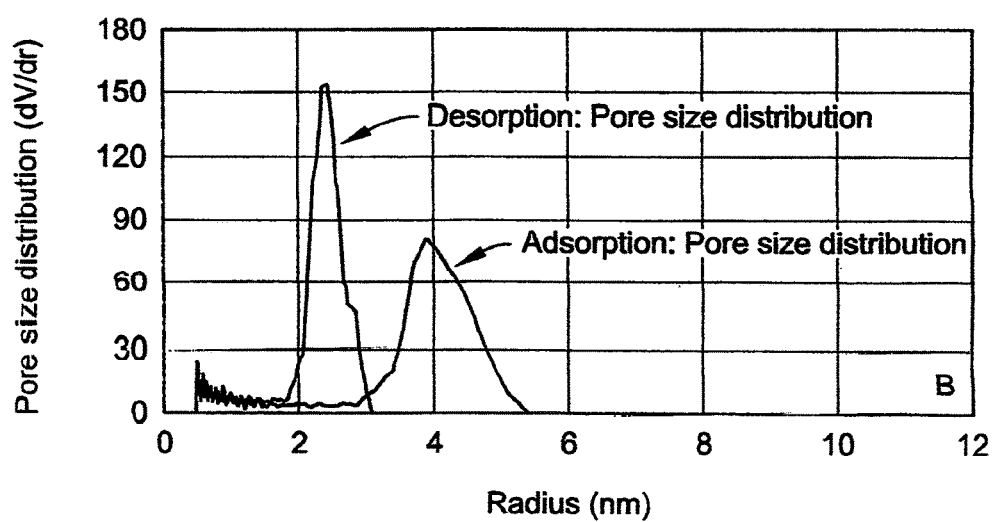

The depolarization parameters $L_j$ can be related to the shape of the "inclusions" within the host material (pores or pore network) and can be a valuable parameter for comparison of several samples. The depolarization parameter $L_z$ for anisotropy along the surface normal is equal or close to 0.333 for isotropic sample properties, <0.333 for elongated inclusions (pore network) along the surface normal, and >0.333 for pore networks which are "compressed" along the surface normal (a schematic representation is shown in FIG. 3. Again, in-plane anisotropy is typically not observed in these samples, i.e., rotation of the sample doesn't change the measurement result. Therefore the "depolarization (x-y split)" is fixed at $0.5*(1-L_z)$.

The ABEMA model can be set up in a way to directly extract the layer thickness, total porosity in % of the sample volume, the % of Accessible pores (typically 100%), and % of Filling of those accessible pores. By limiting the last two parameters between 0% and 100%, we can make sure that the resulting fit results are physically reasonable (Example: Let the Total Porosity be 40% and the number of accessible pore be 50%, then a filling of 50% of the accessible pores means that 25% all pores are filled with solvent or in other words, 10% of the effective material is solvent). Potential grading of a model parameter such as the total porosity throughout a porous film can be easily accounted for by using established grading models.

The novel method proposed here uses the ABEMA approach in order to analyze the dynamic ellipsometry or intensity data vs. relative pressure as obtained during an adsorption/desorption cycle. Instead of analyzing each time slice individually as during the Lorentz-Lorenz approach, all or a larger subset of time slices are analyzed simultaneously. Model parameters which are not expected to change during an adsorption/desorption cycle, such as total porosity, % accessible pores, depolarization factors, and skeletal optical properties, are assumed to be the same for each time slice while allowing dynamically changing model parameters to be varied individually for each time slice, e.g., the condensed solvent volume within the pores and the thickness of a porous film. (Simultaneously analyzing data sets obtained on samples of significantly different structural properties while assuming identical optical properties is called a multi-sample analysis. This approach utilizes the significant increase of information content by simultaneously analyzing multiple significantly different experimental data sets while only marginally increasing the model complexity. This approach improves the model sensitivity while de-correlating otherwise correlated model parameters.)

Analogue to a multi-sample analysis, the multi-time slice analysis proposed here utilizes the significant change in the ellipsometric or intensity data caused by the variation of the optical properties of the sample as a result of solvent condensation in the pores. The problem of finding unique model parameters during regression analysis (changing model parameters while comparing model and experimental data in order to find best match) is well overdetermined in this case and allows not only the extraction of the dynamic change in constituent fractions, i.e., condensed solvent volume within the pores, but also the refractive index of the skeletal material. The multi-time slice analysis averages the static model parameters over all time slices and therefore reduces the influence of noise and model inaccuracies for individual time slices on the obtained model parameters. The ABEMA model is further suitable for matching the experimental data accurately over the entire studied spectral range by accounting for potential anisotropy and graded properties of the sample. The anisotropy-related depolarization parameter $L_z$ provides an additional measure to compare the structural quality of different samples. No assumptions need to be made about the filling of pores at a certain relative pressure value. Further, inaccessible pore volume can be included as a model parameter if the skeletal refractive index is known. Relevant result of the model analysis related to porous sample properties directly obtained from the proposed model approach are total porosity, condensed solvent volume vs. relative pressure, thickness of the porous film, anisotropy (depolarization parameter), inaccessible pore volume (optional), skeletal material refractive index, and optional graded properties such as total porosity (optional). The pore size distribution can be obtained as described in Section 1 from the solvent volume vs. relative pressure curves.

Figure 2:
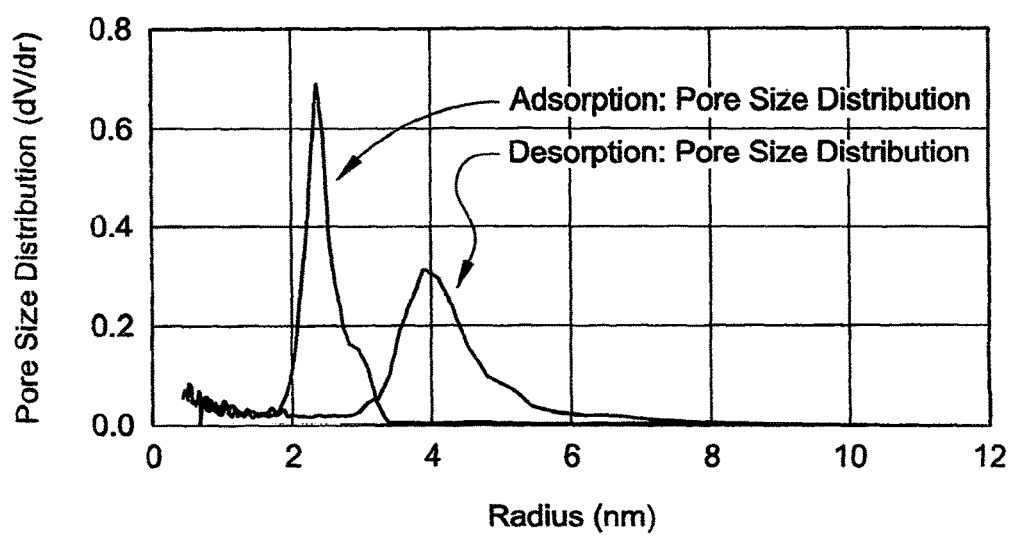
FIG. 2 shows Pore size distribution for the example of porous $SiO_2$ on Si shown in FIG. 1.

Advantages of the anisotropic Bruggeman EMA approach:
  Well established theory to describe effective mediums over wide spectral range, based on physically reasonable model assumptions
  Easily extendable to more constituents
  Depolarization factors represent anisotropic geometries, therefore suitable for more general samples, e.g., anisotropic pores or columnar thin films
  Allows determination of the skeletal material refractive index
  Sensitive to isolated (inaccessible) pore volume (if skeletal n known)
  Can be easily graded for relevant structural parameters such as total porosity Demonstration of the Novel Method by Analyzing a Porous $SiO_2$ Film on Si Substrate To begin, recall from the Background Section that FIG. 1 shows typical hysteresis of the adsorbed solvent (water) volume for an adsorption/desorption cycle on a mesoporous SiO2 film on Si, and that FIG. 2 shows Pore size distribution for the example of porous SiO2 on Si shown in FIG. 1. Also note that FIG. 3 shows an exaggerated and idealized schematic representation of the pore or pore network shape for different depolarization parameter values.

Continuing, in order to obtain information about a porous $SiO_2$ film on Si substrate the following steps were performed:

1. Repeated measurements were performed in-situ while the sample was exposed to a controlled environment of water vapor with specific partial pressure P relative to the saturation vapor pressure of water for flat surfaces P0, i.e., the relative pressure P/P0 was cycled between 0.1 and 0.9, (See FIG. 4).

2. Forty time slices, equally separated over an entire Adsorption/Desorption cycle, were selected for simultaneous analysis, (See FIG. 5).

3. An anisotropic Bruggeman effective medium model was developed in order to allow determination of the total porosity, depolarization factor Lz, the % of accessible pores ("% Accessible"), the % of those accessible pores which are filled at a certain relative pressure value ("% Filling"), the thickness of the porous layer, the grading profile of the total porosity over the entire thickness, and the refractive index of the skeletal material ("Gen-Osc"), (See FIG. 6). During the regression analysis, the parameters "% Filling" and Thickness were allowed to be varied for each time slice while all other parameters were assumed to be identical for each time slice.

4. The skeletal refractive index, the anisotropy related depolarization factor Lz, the total porosity, and the total porosity grading profile are direct results of the multiple-time slice analysis (See FIGS. 7A and 7B) as well as the film thickness and "% Filling" parameter for each time slice. (See FIGS. 8A and 8B).

5. The pore size distribution can be obtained as derivative of the condensed solvent volume within the pores vs. relative pressure. The Kelvin equation (Eq. (1)) is used to assign a specific pore radius value to each relative pressure value.

Figure 9C:
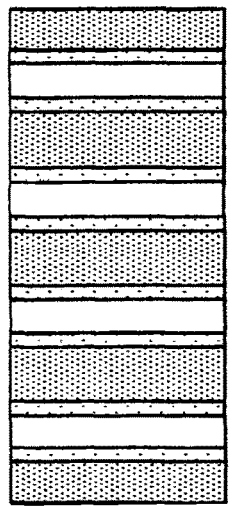
FIGS. 9A, 9B and 9C show, respectively, pictorial representations of, respectively.
Figure 9B:
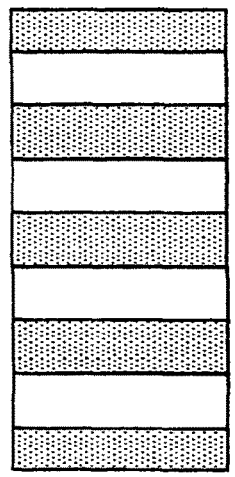
Figure 9A:
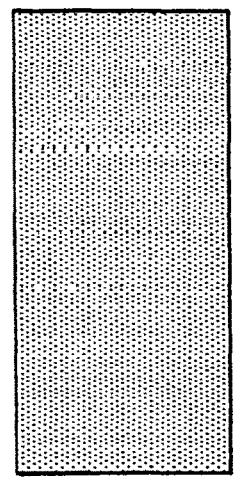

FIGS. 9A, 9B and 9C show pictorial representations of, respectively:

$$P = \frac{n_s^2 - 1}{n_s^2 + 2};$$

$$P = \frac{n_e^2 - 1}{n_e^2 + 2} = V_1 \frac{n_0^2 - 1}{n_0^2 + 2} + (1 - V_1) \frac{n_s^2 - 1}{n_s^2 + 2}; = (1 - V) \frac{n_s^2 - 1}{n_s^2 + 2};$$

and $$P\left(\frac{p}{p_0}\right) = \frac{n_{rel}^2 - 1}{n_{rel}^2 + 2} = V_1 \frac{n_0^2 - 1}{n_0^2 + 2} + V_2 \frac{n_{sol}^2 - 1}{n_{sol}^2 + 2} + (1 - V_1 - V_2) \frac{n_s^2 - 1}{n_s^2 + 2};$$

Where V . . . is the Total porosity.

In the Claims it is to be understood that an ellipsometer system can be operated so as to obtain intensity data, although foregoing the phase angle data usually provides less accurate and reliable results. It is further noted that where a Claim recites that differentiation is performed, this can take the form of numerical differentiation. It is to be appreciated that Numerical differentiation can enter large changes in the end results, based on small changes in the source data. Therefore, where source data is accessed, it is to be understood that it can be subject to smoothing, or parameterization, (which can take the form of, for instance, fitting some mathematical function to the curves in FIG. 8A). For insight, if FIG. 8B date were to be numerically integrated, the curves therein could be parameterized to provide Gaussian curves, which upon numerical integration would then provide smoother FIG. 8A curves. In fact either FIG. 8A or 8B could be obtained by regression onto data, and differentiation or integration then performed to arrive at FIG. 8B or 8A data, respectively.

Having hereby disclosed the subject matter of the present invention, it should be apparent that many modifications, substitutions and variations of the present invention are possible in view of the teachings. It is therefore to be understood that the invention may be practiced other than as specifically described and should be limited in its breadth and scope only by the Claims.

We claim:

1. A method of determining the distribution of pore size distribution vs. radius in a porous sample selected from the group consisting of:
   1) a porous thin film having an effective thin layer thickness and a surface; and
   2) a porous surface region of a semi-infinite bulk substrate having a surface;

Said method comprising the steps of:
   a) providing a selection from the group consisting of:
      1) a reflectometer comprising a source of electromagnetic radiation, a stage for supporting a sample and a detector of electromagnetic radiation; and
      2) an ellipsometer or polarimeter comprising a source of electromagnetic radiation, a polarizer, a stage for supporting a sample, an analyzer and a detector of electromagnetic radiation, said ellipsometer or polarimeter optionally comprising at least one compensator between said source and detector;
   b) placing a selected sample on said stage and while causing said surface of said sample to undergo a sequential plurality of solvent relative pressures, causing said selected reflectometer, ellipsometer or polarimeter to direct a beam of electromagnetic radiation at said sample, so that it interacts therewith and enters said detector which mediates the development of a set of reflectometer or ellipsometer or polarimeter data;
   c) before, after or simultaneous with step b) providing a mathematical model of said selected sample which includes as parameters a plurality of filling fractions as a function of solvent relative pressure;
   d) performing a regression procedure of said mathematical model provided in step c) onto at least some of said data determined in step b) to determine data corresponding to an effective plot of filling fraction vs. solvent relative pressures;
   e) performing a differentiation of said effective plot of filling fraction vs. solvent relative pressures determined in step d), to provide an effective plot of pore size distribution vs. radius.

2. A method of determining the distribution of pore size distribution vs. radius in a porous sample selected from the group consisting of:
   1) a porous thin film having an effective thin layer thickness and a surface; and
   2) a porous surface region of a semi-infinite bulk substrate having a surface;

said method comprising the steps of:
   a) providing a selection from the group consisting of:
      1) a reflectometer comprising a source of electromagnetic radiation, a stage for supporting a sample and a detector of electromagnetic radiation; and
      2) an ellipsometer or polarimeter comprising a source of electromagnetic radiation, a polarizer, a stage for supporting a sample, an analyzer and a detector of electromagnetic radiation, said ellipsometer or polarimeter optionally comprising at, least one compensator between said source and detector;
   b) placing a selected sample on said stage and while causing said surface of said sample to undergo a sequential plurality of solvent relative pressures, causing said selected reflectometer, ellipsometer or polarimeter to direct a beam of electromagnetic radiation at said sample, so that it interacts therewith and enters said detector which mediates the development of a set of reflectometer or ellipsometer or polarimeter data;

c) before, after or simultaneous with step b) providing a mathematical model of said selected sample which includes as parameters a plurality of filling fractions as a function of solvent relative pressure, and further provides a parameterized representation of an effective plot of pore size distribution vs. radius;

d) performing a regression procedure of said mathematical model provided in step c) onto at least some of said data determined in step b) to simultaneously determine best fit values for the parameters in said effective plot of pore size distribution vs. radius, and an effective plot of filling fraction vs. solvent relative pressures which is arrived at by an integration of said parameterized representation of an effective plot of pore size distribution vs. radius, during said regression.

3. A method as in claim 1 or 2 wherein said sample comprises skeletal material presenting with a total volumetric porosity %, a % of total pores present in the volume of said thin film which are accessible by solvent presented at said surface thereof, and a % of accessible pores actually filled with solvent at a plurality of times during which the partial pressure of said solvent, relative to the saturation vapor pressure of said solvent over any flat surface, is changed at said sample surface, and wherein the mathematical model of said sample is a Bruggeman effective medium model including as parameters therein, at least:

variable wavelength dependent refractive index of said skeletal material;
variable total porosity %;
variable % of accessible pores that are filled with solvent at a given partial pressure, (ie. volume filling plot); and
wavelength dependent refractive index values of said solvent;
wherein while assuming fixed values for wavelength dependent solvent refractive indices, and for at least one selection from the group consisting of:
100% of all pores are assumed accessible; and
the wavelength dependent refractive indices of said skeletal material are known.

4. A method as in claim 1 or 2 wherein said sample comprises skeletal material presenting with a total volumetric porosity %, a % of total pores present in the volume of said thin film which are accessible by solvent presented at said surface thereof, and a % of accessible pores actually filled with solvent at a plurality of times during which the partial pressure of said solvent, relative to the saturation vapor pressure of said solvent over any flat surface, is changed at said sample surface, and wherein the mathematical model of said sample is a Bruggeman effective medium model including as parameters therein, at least:

variable wavelength dependent refractive index of said skeletal material;
variable total porosity %;
variable % of accessible pores that are filled with solvent at a given partial pressure, (ie. volume filling plot); and
wavelength dependent refractive index values of said solvent;
and at least one additional parameter selected from the group consisting of:
variable % of accessible pores;
if the sample is a thin film, a thickness parameter therefore; and/or
variable grading profile of any of the mathematical model parameters over the investigated thickness of said sample; and/or
at least one variable depolarization factor; and
wherein while assuming fixed values for wavelength dependent solvent refractive indices, and for at least one selection from the group consisting of:
100% of all pores are assumed accessible; and
the wavelength dependent refractive indices of said skeletal material are known.

5. A method as in claim 1 or 2 in which the plurality of ellipsometric or intensity data sets obtained in step b) are spectroscopic and the regression in step d) involves at least two thereof for each of said plurality of ellipsometric or intensity data sets that correspond to a plurality of times corresponding to different solvent partial pressures being presented to the surface of said sample.

6. A method as in claim 1 or 2 in which the plurality of ellipsometric or intensity data sets obtained in step b) are obtained during solvent adsorption or desorption within the sample pores for a plurality of times during which the partial pressure of said solvent is increased or decreased at said sample surface respectively, or during an adsorption-desorption hysteresis cycle during which the partial pressure of said solvent is increased and decreased at said sample surface.

7. A method as in claim 1 or 2 in which the plurality of ellipsometric or intensity data sets obtained in step b) are obtained during solvent adsorption or desorption at said sample surface for a plurality of times during which the partial pressure of said solvent is increased or decreased at said sample surface respectively, which further comprises determining pore size distribution involving use of a derivative of a volume filling plot vs. partial pressure.

8. A method as in claim 1 or 2 in which data is obtained in step b) during an adsorption-desorption hysteresis cycle during which the partial pressure of said solvent is both increased and decreased at said sample surface within a partial range between zero and saturation partial pressure.

9. A method as in claim 1 or 2 in which data is obtained in step b) during an adsorption-desorption hysteresis cycle during which the partial pressure of said solvent is both increased and decreased at said sample surface within a full range between zero and saturation partial pressure, at which none, and at which all pores are filled, respectively.

10. A method as in claim 1 or 2 in which variable grading profile of any of the mathematical model parameters over the investigated thickness of said sample; and/or a variable depolarization factor are included in the model if that inclusion provides better fit of parameters when said step d) regression is performed.

11. A method as in claim 1 or 2 in which the wavelength dependent values of skeletal material refractive index are known and fixed, and variable % of accessible pores is a variable, or in which the wavelength dependent values of skeletal material refractive index are variable, and variable % of accessible pores is fixed and the remaining variable parameters are fit parameters.

12. A method as in claim 1 or 2 in which the wavelength dependent values of skeletal material refractive index are fixed, 100% of pores are assumed accessible, and the remaining variable parameters are fit parameters.

13. A method as in claim 1 or 2 wherein the mathematical model provided in step e) further provides that said selected sample is modeled as comprising a plurality of layers, each said layer being characterized by at least one parameter which is separately evaluated in step d) to the same as, or different from those of other layers.

14. A method as in claim 1 or 2 wherein the mathematical model provided in step c) further provides that said selected sample is modeled as comprising a plurality of layers, each said layer being characterized by at least one parameter which is separately evaluated in step d) to be:

the same as; or different from those in other layers;

thereby providing a graded relationship of said at least one parameter as a function of layer position in said sample, said layers each including as said at least one parameter, at least one selection from the group consisting of:

total porosity;

% of accessible pores; and depolarization factor.

\* \* \* \* \*